US012611223B2

(12) United States Patent
Kojima et al.

(10) Patent No.: US 12,611,223 B2
(45) Date of Patent: Apr. 28, 2026

(54) BALLOON FOR BALLOON CATHETER

(71) Applicant: KANEKA CORPORATION, Osaka (JP)

(72) Inventors: Masahiro Kojima, Settsu (JP); Masato Tsueda, Settsu (JP); Yoshinori Nakano, Settsu (JP); Takahisa Hamabuchi, Osaka (JP)

(73) Assignee: KANEKA CORPORATION, Osaka (JP)

( * ) Notice: Subject to any disclaimer, the term of this patent is extended or adjusted under 35 U.S.C. 154(b) by 490 days.

(21) Appl. No.: 18/279,105

(22) PCT Filed: Feb. 4, 2022

(86) PCT No.: PCT/JP2022/004419
§ 371 (c)(1),
(2) Date: Aug. 28, 2023

(87) PCT Pub. No.: WO2022/196166
PCT Pub. Date: Sep. 22, 2022

(65) Prior Publication Data
US 2024/0149025 A1 May 9, 2024

(30) Foreign Application Priority Data

Mar. 15, 2021 (JP) ................................. 2021-041378

(51) Int. Cl.
*A61B 17/3207* (2006.01)
*A61M 25/10* (2013.01)
(52) U.S. Cl.
CPC . *A61B 17/320725* (2013.01); *A61M 25/1002* (2013.01); *A61M 25/104* (2013.01); *A61M 2025/1086* (2013.01)

(58) Field of Classification Search
CPC ............... A61B 17/320725; A61M 2025/1086
See application file for complete search history.

(56) References Cited

U.S. PATENT DOCUMENTS 5,196,024 A * 3/1993 Barath ........... A61B 17/320725
606/191
2009/0234283 A1 9/2009 Burton et al.
(Continued)

FOREIGN PATENT DOCUMENTS

CN 109893215 A 6/2019
JP 2011-513031 A 4/2011
(Continued)

OTHER PUBLICATIONS

International Search Report, issued in PCT/JP2022/004419, PCT/ISA/210, dated Mar. 15, 2022.

*Primary Examiner* — William R Carpenter
(74) *Attorney, Agent, or Firm* — Birch, Stewart, Kolasch & Birch, LLP

(57) ABSTRACT

Provided is a balloon for a balloon catheter that is easy to insert in a body cavity, has good pushability, and can easily incise a stenosis. A balloon for a balloon catheter, having a balloon body (20), the balloon body (20) having a protrusion part (60) that projects outwardly in the radial direction y from its outer surface in the straight tubular part (23) and the proximal tapered part (22), wherein a ratio $W_1/H_1$ of a height $H_1$ of the protrusion part (60) and a width $W_1$ of the protrusion part (60) in the straight tubular part (23) is greater than a ratio $W_2/H_2$ of a height $H_2$ of the protrusion part (60) and a width $W_2$ of the protrusion part (60) in the proximal tapered part (22).

12 Claims, 6 Drawing Sheets

(56) References Cited

U.S. PATENT DOCUMENTS

| | | | |
|---|---|---|---|
| 2012/0130407 A1* | 5/2012 | Aggerholm | A61B 17/320725 |
| | | | 606/159 |
| 2012/0215251 A1 | 8/2012 | Burton et al. | |
| 2016/0058982 A1 | 3/2016 | Aggerholm et al. | |
| 2017/0112526 A1 | 4/2017 | Burton et al. | |
| 2018/0296241 A1 | 10/2018 | Burton et al. | |
| 2021/0113820 A1 | 4/2021 | Okamoto et al. | |
| 2021/0113821 A1 | 4/2021 | Okamoto et al. | |

FOREIGN PATENT DOCUMENTS

| | | | | |
|---|---|---|---|---|
| WO | WO-2018060466 A1 * | 4/2018 | .......... | A61M 25/104 |
| WO | WO 2020/012850 A1 | 1/2020 | | |
| WO | WO 2020/012851 A1 | 1/2020 | | |
| WO | WO-2022102766 A1 * | 5/2022 | .......... | A61M 25/104 |

* cited by examiner

[FIG. 1]
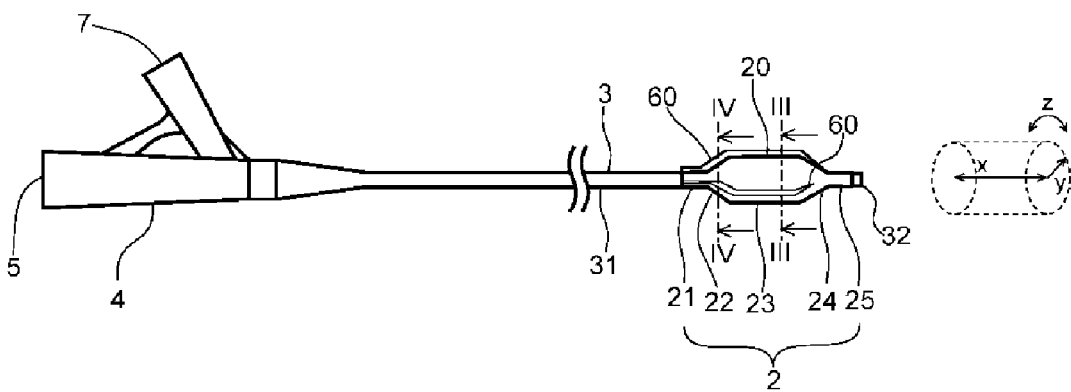
[FIG. 2]
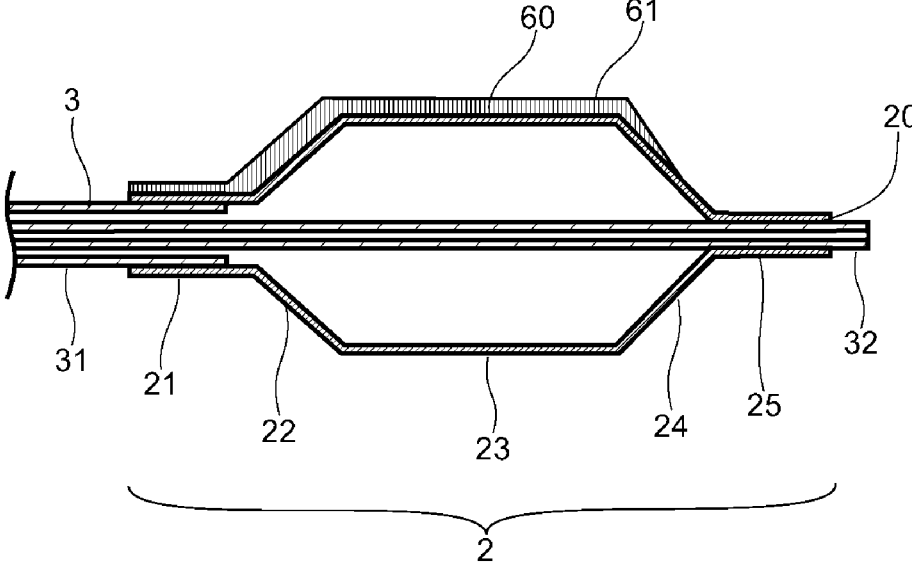

[FIG. 3]
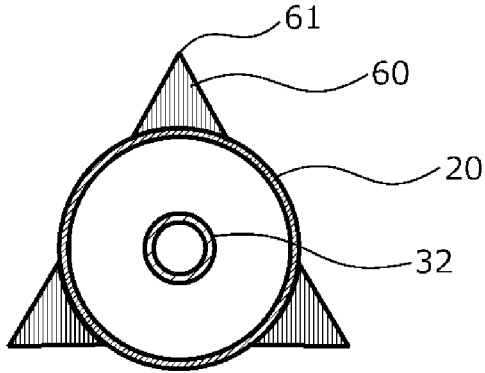
[FIG. 4]
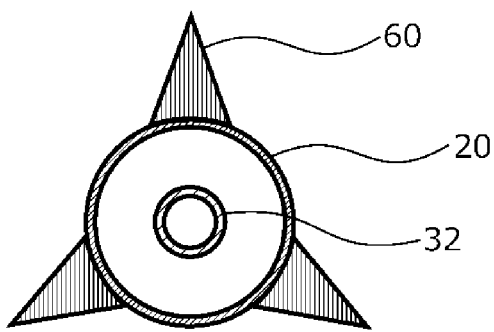
[FIG. 5]
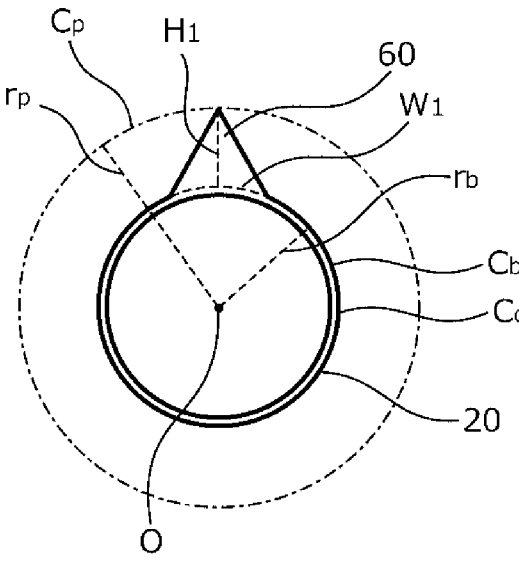

[FIG. 6]
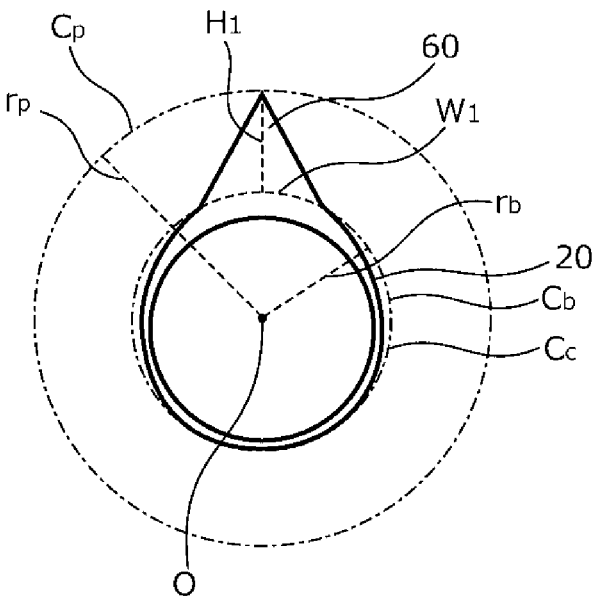
[FIG. 7]
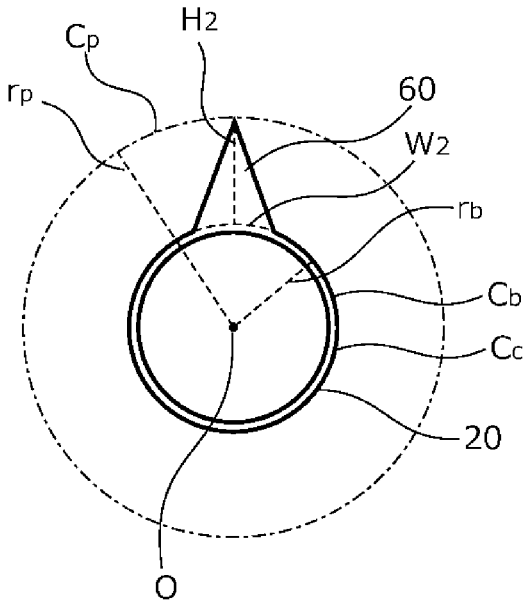

[FIG. 8]
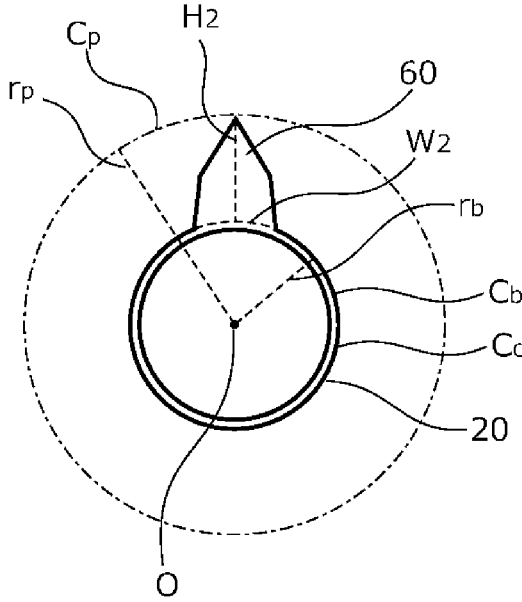
[FIG. 9]
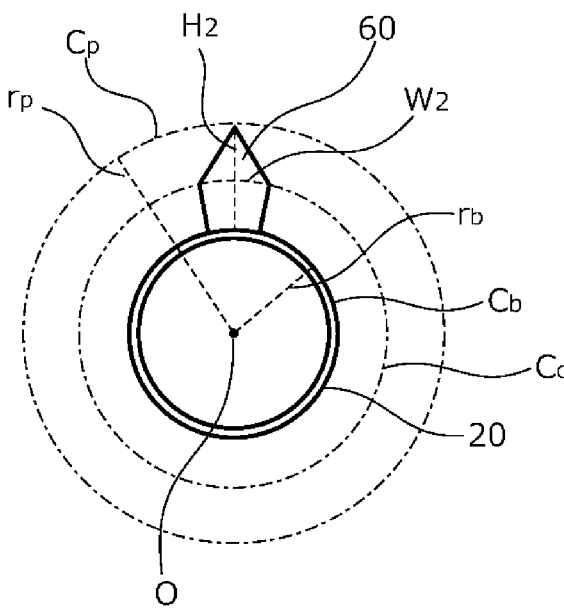

[FIG. 10]
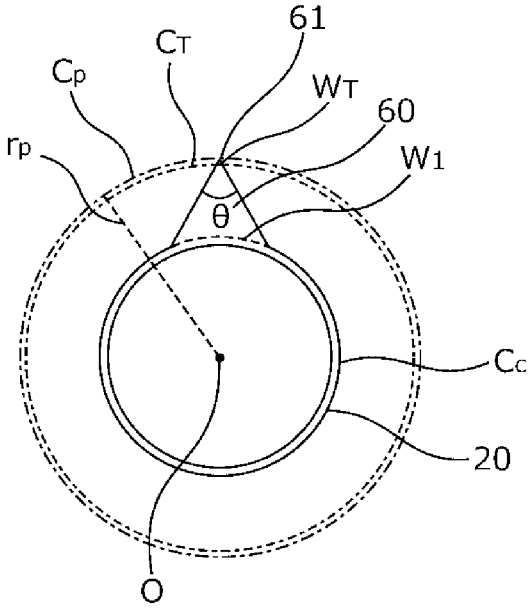
[FIG. 11]
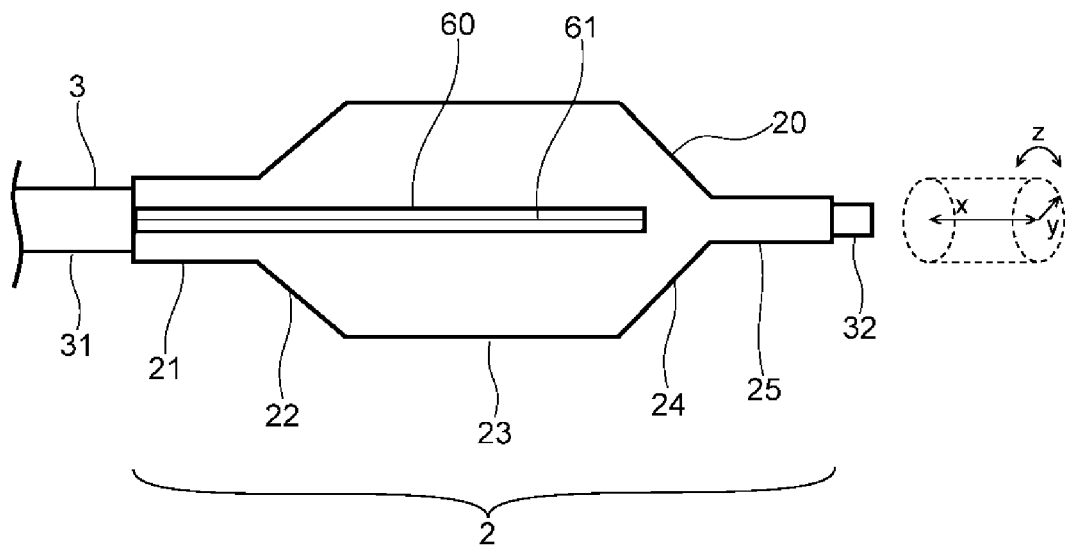

[FIG. 12]
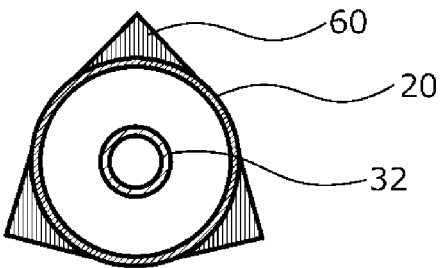
[FIG. 13]
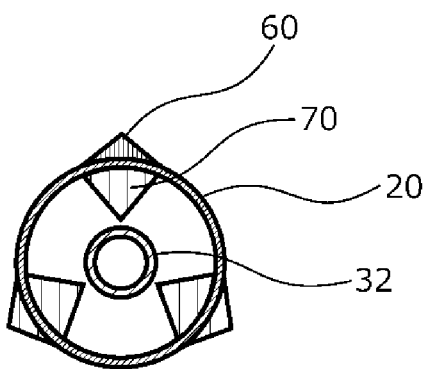
[FIG. 14]
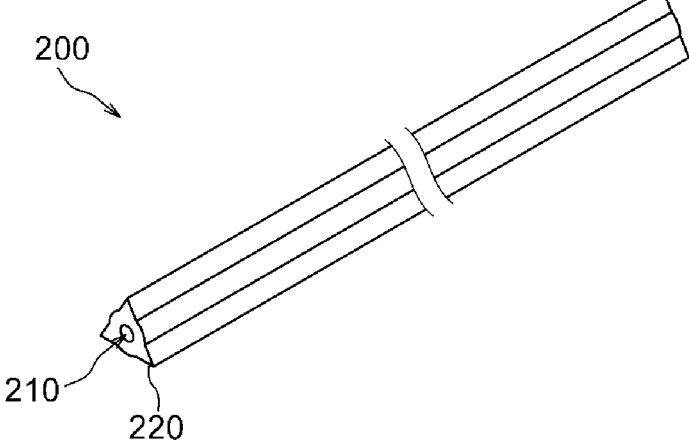

BALLOON FOR BALLOON CATHETER

TECHNICAL FIELD

The present invention relates to a balloon for a balloon catheter.

BACKGROUND ART

Diseases such as angina pectoris and myocardial infarction are caused by the formation of stenotic areas hardened by calcification and other factors in the inner walls of blood vessels. One of treatments for these diseases is angioplasty, in which a balloon catheter is used to dilate the stenotic area. Angioplasty is a minimally invasive therapy that does not require an open chest procedure like bypass surgery, and is widely used.

In angioplasty, it is sometimes difficult to dilate a stenosis that has hardened due to calcification and other factors with a standard balloon catheter. In some cases, while the method of dilating a stenosis by implanting an indwelling expansion device called a stent into the stenosis is also used, an ISR (In-Stent-Restenosis) lesion, for example, may occur after this treatment, in which the neointima of the vessel grows excessively and the vessel becomes stenotic again. The neointima in ISR lesions is soft and the surface is slippery, so a standard balloon catheter may cause the balloon to shift out of the lesion site to damage the vessel when the balloon is inflated.

As balloon catheters that can dilate a stenosis even in such calcified or ISR lesions, balloon catheters with a protrusion, blade, or scoring element on the balloon to bite into the stenosis have been developed. For example, Patent document 1 discloses a balloon catheter in which protrusion located in the distal tapered part is higher than protrusion located in the straight tubular part. Patent document 2 discloses a balloon catheter in which a dilating element connected to the outer surface of the balloon with a connector has a first effective width and a second effective width, and the first effective width is less than the second effective width.

RELATED ART DOCUMENT

Patent Document

Patent Document 1: WO2020/012850
Patent Document 2: JP 2011-513031 T

SUMMARY OF THE INVENTION

Problems to be Solved by the Invention

A balloon catheter is inserted into a body cavity in a deflated state and delivered to the treatment site through the body cavity. When delivered, the delivery of the balloon is controlled by transmitting operations from the hand side to the tip side where the balloon is positioned. At this time, easy insertion in the body cavity and easy transmission of the operation from the hand side to the tip side (high pushability) can improve treatment safely and shorten treatment time, enabling treatment less burden on the patient. In addition, after the balloon is delivered to the treatment site, it is required to efficiently and easily incise the stenosis. However, conventional balloon catheters have room for improvement in terms of ease of insertion in the body cavity, pushability, and ease of incision of the stenosis.

In view of the above circumstances, the objective of the present invention is to provide a balloon for a balloon catheter that is easy to insert in a body cavity, has good pushability, and can easily incise a stenosis.

Means for Solving the Problems

A balloon for a balloon catheter in accordance with one embodiment of the present invention that can solve the above problems comprises a balloon body having an outer surface and an inner surface; a longitudinal axis direction, a radial direction connecting a point on the outer surface and a center of a figure whose outline is an outer shape of the balloon body in an inflated state in a cross section perpendicular to the longitudinal axis direction, and a circumferential direction along an outer perimeter of the balloon body in the inflated state in a cross section in the radial direction, wherein the balloon body has a straight tubular part, a proximal tapered part located proximal to the straight tubular part, and a distal tapered part located distal to the straight tubular part; the balloon body has a protrusion part that projects outwardly in the radial direction from the outer surface of the balloon body and extends in the longitudinal axis direction in the straight tubular part and the proximal tapered part; a ratio $W_1/H_1$ of a height $H_1$ of the protrusion part and a width $W_1$ of the protrusion part in the straight tubular part is greater than a ratio $W_2/H_2$ of a height $H_2$ of the protrusion part and a width $W_2$ of the protrusion part in the proximal tapered part.

(The definition of the height and the width of the protrusion part is as follows:

the height of the protrusion part is a difference between a radius of a circumscribed circle $C_b$, of the balloon body and a radius of a circumscribed circle $C_p$ of the protrusion part that shares a center with the circumscribed circle $C_b$ in the radial cross section;

and the width of the protrusion part is a maximum length of an arc inside an outline of the protrusion part among circumferences of concentric circles that share a center with the circumscribed circle $C_b$.)

Preferably, the width $W_1$ of the protrusion part in the straight tubular part is wider than the width $W_2$ of the protrusion part in the proximal tapered part.

Preferably, the ratio $W_1/H_1$ in the straight tubular part is 0.2 or greater and 5 or smaller.

Preferably, the ratio $W_2/H_2$ in the proximal tapered part is 0.2 or greater and 5 or smaller.

Preferably, the protrusion part of the straight tubular part has a tip part in the radial cross section, and a ratio $W_1/H_1$ of a width $W_T$ of the tip part of the protrusion part and the width $W_1$ of the protrusion part is 0.5 or smaller.

(The definition of the width of the tip part of the protrusion part is as follows:

the width of the tip part of the protrusion part is a length of an arc that is inside the outline of the protrusion part and is a part of a circumference of a concentric circle that has a radius 95% of the radius of the circumscribed circle $C_p$ and shares the center with the circumscribed circle $C_p$ in the radial cross section.)

Preferably, the height $H_1$ of the protrusion part of the straight tubular part is at least 0.1 mm or higher.

Preferably, the protrusion part of the straight tubular part has a tip part in the radial cross section, and the tip part has an angle of 135° or less.

Preferably, the protrusion part of the straight tubular part and the protrusion part of the proximal tapered part extend continuously in the longitudinal axis direction.

Preferably, the distal tapered part has the protrusion part, and a height $H_3$ of the protrusion part of the distal tapered part is lower than the height $H_1$ of the protrusion part of the straight tubular part. In this case, preferably, the protrusion part of the straight tubular part and the protrusion part of the distal tapered part extend continuously in the longitudinal axis direction.

Preferably, the distal tapered part has an inner protrusion part that projects inwardly in the radial direction from the inner surface of the balloon body and extends in the longitudinal axis direction. In this case, preferably, the distal tapered part has the protrusion part, and the protrusion part and the inner protrusion part of the distal tapered part are arranged in the same position in the circumferential direction.

Preferably, the protrusion part s composed of the same material as the balloon body.

Effects of the Invention

The above balloon for a balloon catheter can be easily inserted in a body cavity, has good pushability, and can easily incise a stenosis, because the ratio $W_1/H_1$ of the height $H_1$ of the protrusion part and the width $W_1$ of the protrusion part in the straight tubular part is greater than the ratio $W_2/H_2$ of the height $H_2$ of the protrusion part and the width $W_2$ of the protrusion part in the proximal tapered part.

BRIEF DESCRIPTION OF THE DRAWINGS

FIG. 1 is a side view of a balloon catheter in accordance with one embodiment of the present invention.

FIG. 2 is a cross-sectional view in the longitudinal direction of the balloon of the balloon catheter shown in FIG. 1 in the inflated state.

FIG. 3 is a III-III cross-sectional view of FIG. 1.

FIG. 4 is a IV-IV cross-sectional view of FIG. 1.

FIG. 5 is a cross-sectional view in the radial direction of the straight tubular part in accordance with another embodiment of the present invention.

FIG. 6 is a cross-sectional view in the radial direction of the straight tubular part in accordance with still another embodiment of the present invention.

FIG. 7 is a cross-sectional view in the radial direction of the proximal tapered part in accordance with another embodiment of the present invention.

FIG. 8 is a cross-sectional view in the radial direction of the proximal tapered part in accordance with still another embodiment of the present invention.

FIG. 9 is a cross-sectional view in the radial direction of the proximal tapered part in accordance with still another embodiment of the present invention.

FIG. 10 is a figure explaining the tip part of the protrusion part in the embodiment shown in FIG. 5.

FIG. 11 is a plan view seeing from the side of the protrusion part of the balloon in accordance with one embodiment of the present invention.

FIG. 12 is a cross-sectional view in the radial direction of the distal tapered part in accordance with one embodiment of the present invention.

FIG. 13 is a cross-sectional view in the radial direction of the distal tapered part in accordance with another embodiment of the present invention.

FIG. 14 is a perspective view of a parison before expansion in accordance with one embodiment of the present invention.

MODE FOR CARRYING OUT THE INVENTION

Hereinafter, the defibrillation catheter and the defibrillation system according to the present invention will be described based on the following embodiments, however, the present invention is not limited by the following embodiments and can be altered in design within a scope in compliance with the intent described above and below, and all the changes are to be encompassed within a technical scope of the present invention. Note that, in each drawing, hatching, reference signs for components, and the like may be omitted for convenience of description, and in such a case, the specification and other drawings are to be referred to. Furthermore, since the dimensions of the various components in the drawings are provided for the purpose of facilitating the understanding of the feature of the present invention, the dimensions may differ from the actual dimensions in some cases.

A balloon for a balloon catheter in accordance with embodiments of the present invention has a balloon body having an outer surface and an inner surface; and has a, longitudinal axis direction, a radial direction connecting a point on the outer surface and a center of a figure whose outline is an outer shape of the balloon body in an inflated state in a cross section perpendicular to the longitudinal axis direction, and a circumferential direction along an outer perimeter of the balloon body in the inflated state in a cross section in the radial direction, wherein the balloon body has a straight tubular part, a proximal tapered part located proximal to the straight tubular part, and a distal tapered part located distal to the straight tubular part; the balloon body has a protrusion part that projects outwardly in the radial direction from the outer surface of the balloon body and extends in the longitudinal axis direction in the straight tubular part and the proximal tapered part; and a ratio $W_1/H_1$ of a height $H_1$ of the protrusion part and a width $W_1$ of the protrusion part in the straight tubular part is greater than a ratio $W_2/H_2$ of a height $H_2$ of the protrusion part and a width $W_2$ of the protrusion part in the proximal tapered part. The definition of the height and width of the protrusion part is as follows:

The height of the protrusion part is a difference between a radius of a circumscribed circle $C_b$ of the balloon body and a radius of a circumscribed circle $C_p$ of the protrusion part that shares a center with the circumscribed circle $C_p$ in the radial cross section.

The width of the protrusion part is a maximum length of an arc inside an outline of the protrusion part among circumferences of concentric circles that shares a center with the circumscribed circle $C_b$ in the radial cross section.

The ratio $W_1/H_1$ of the height $H_1$ of the protrusion part and the width $W_1$ of the protrusion part in the straight tubular part is greater than the ratio $W_2/H_2$ of the height $H_2$ of the protrusion part and the width $W_2$ of the protrusion part in the proximal tapered part, allowing the balloon to efficiently incise the stenosis when inflated. This is thought to be because by satisfying the above relationship, the width $W_1$ of the protrusion part of the straight tubular part can be relatively larger than the height $H_1$, thereby widening the area that can be incised by the protrusion part in the circumferential direction z and increasing the dilating force during incision. In addition, the ratio $W_1/H_1$ of the height $H_1$ and the width $W_1$ of the protrusion part in the straight tubular part is relatively greater, that is, the height $H_1$ of the protrusion part is relatively smaller than the width $W_1$, thereby allowing the outer diameter of the balloon when deflated to be relatively small and facilitating insertion of the balloon into the body cavity. Furthermore, the deflation time is shortened because the stiffness of the balloon is reduced to facilitate balloon deflation, shortening the treatment time when multiple dilatations are performed and reducing the time required to remove the deflated balloon after dilatation or to transport it to another lesion, resulting in safer and less burdensome treatment for the patient.

The ratio $W_1/H_1$ of the height $H_1$ of the protrusion part and the width $W_1$ of the protrusion part in the straight tubular part is greater than the ratio $W_2/H_2$ of the height $H_2$ of the protrusion part and the width $W_2$ of the protrusion part in the proximal tapered part, that is, the ratio $W_2/H_2$ of the height $H_2$ and the width $W_2$ of the protrusion part in the proximal tapered part is relatively small, allowing the height $H_2$ of the protrusion part in the proximal tapered part to be relatively larger than the width $W_2$. This allows the balloon to have good pushability by increasing the bending stiffness of the proximal tapered part compared to the straight tubular part. In addition, the ratio $W_2/W_2$ of the height $H_2$ and the width $W_2$ of the protrusion part in the proximal tapered part is relatively small, that is, the width $W_2$ of the protrusion part is relatively smaller than the height $H_2$, which narrows the area that is a three-dimensional obstacle in the circumferential direction when the balloon is inserted into the body cavity, facilitating insertion of the balloon in the body cavity.

Thus, the balloon of the present invention can decrease its bending stiffness in the longitudinal axis direction from the proximal to the distal side of the balloon, so that the balloon as a whole has an optimal balance of bending stiffness, allowing the balloon to have good pushability and also good king resistance and insertion properties.

Referring to FIG. 1 to FIG. 14, the balloon for a balloon catheter will be explained. FIG. 1 is a side view of a balloon catheter in accordance with one embodiment of the present invention. FIG. 2 is a cross-sectional view in the longitudinal direction of the balloon of the balloon catheter shown in FIG. 1 in the inflated state. FIG. 3 is a III-III cross-sectional view of FIG. 1, and FIG. 4 is a IV-IV cross-sectional view of FIG. 1. FIG. 5 is a cross-sectional view in the radial direction of the straight tubular part in accordance with another embodiment of the present invention, and FIG. 6 is a cross-sectional view in the radial direction of the straight tubular part in accordance with still another embodiment of the present invention. FIGS. 7 to 9 are cross-sectional views in the radial direction of the proximal tapered part in accordance with different embodiments of the present invention, respectively. FIG. 10 is a figure explaining the tip part of the protrusion part in the embodiment shown in FIG. 5. In FIGS. 5 to 10, the inner tube and hatching are omitted for clarity in explaining the height and width of the protrusion part. FIG. 11 is a plan view seeing from the side of the protrusion part of the balloon in accordance with one embodiment of the present invention. FIG. 12 is a cross-sectional view in the radial direction of the distal tapered part in accordance with one embodiment of the present invention, and FIG. 13 is a cross-sectional view in the radial direction of the distal tapered part in accordance with another embodiment of the present invention. FIG. 14 is a perspective view of a prison before expansion in accordance with one embodiment of the present invention.

In the present invention, a proximal side refers to the direction towards a user's or operator's hand in the extending direction of a balloon catheter 1 or a longitudinal axis direction x of a shaft 3, and a distal side refers to the opposite side of the proximal side, that is, the direction towards the person to be treated. Members other than long-shaped members, such as the shaft 3, also has the same longitudinal axis direction x as the shaft 3.

As shown in FIG. 1 and FIG. 2, the balloon catheter 1 has the shaft 3 and a balloon 2 for a balloon catheter disposed outside the shaft 3. The balloon catheter 1 has the distal side and the proximal side, and the balloon 2 is disposed on the distal side of the shaft 3. The balloon catheter 1 is configured such that fluid is introduced in the balloon 2 through the shaft 3, and the inflation and deflation of the balloon 2 can be controlled using an indeflator (pressurizer for balloons). The fluid may be a pressurized fluid pressurized by a pump or the like.

The shaft 3 preferably has a flow path fix the fluid inside, and further has a guidewire insertion path. Configurations in which the shaft 3 has an internal fluid path and guidewire insertion path include, for example, a configuration in which the shaft 3 has an outer tribe 31 and an inner tube 32, and the inner tube 32 serves as the guidewire insertion path and the space between the inner tube 32 and the outer tube 31 serves as the fluid flow path. In the case where the shaft 3 has the outer tube 31 and the inner tube 32, preferably, the inner tube 32 extends through the distal end of the outer tube 31 and penetrates the balloon 2 to the distal side, the distal side of the balloon 2 is fixed to the inner tube 32, and the proximal side of the balloon 2 is fixed to the outer tube 31.

As shown in FIG. 1 and FIG. 2, the balloon 2 has a balloon body 20 having an outer surface and an inner surface, and has the longitudinal axis direction x, a radial direction y connecting a point on the outer surface and the center of a figure whose outline is the outer shape of the balloon body 20 in the inflated state in a cross section perpendicular to the longitudinal axis direction x, and a circumferential direction z along the outer perimeter of the balloon body 20 in the inflated state in a cross section in the radial direction y.

The balloon body 20 has a straight tubular part 23, a proximal tapered part 22 located proximal to the straight tubular part 23, and a distal tapered part 24 located distal to the straight tubular part 23. The straight tubular part 23 preferably has approximately the same diameter along the longitudinal axis direction x, and the proximal tapered part 22 and the distal tapered part 24 are preferably formed so that the diameter decreases as it is away from the straight tubular part 23. The straight tubular part 23 having the largest diameter can make sufficient contact with the lesion to facilitate dilatation or incise of the lesion when the balloon 2 is inflated at the lesion such as stenosis. The proximal tapered part 22 and the distal tapered part 24, the diameter of which is decreased, can decrease the outer diameter of the proximal end part and the distal end part of the balloon 2 to reduce the step between the shaft 3 and the balloon 2 when the balloon 2 is deflated, thereby allowing the balloon 2 to be easily inserted into the body cavity.

The balloon 2 may have a proximal sleeve part 21 and a distal sleeve part 25, which are non-inflatable, on the side proximal to the proximal tapered part 22 and distal to the distal tapered part 24, respectively. At least a part of the proximal sleeve part 21 and the distal sleeve part 25 can be fixed to the shaft 3. When the shaft 3 has the outer tube 31 and the inner tube 32, at least a part of the proximal sleeve part 21 can be fixed to the outer tube 31, and at least a part of the distal sleeve part 25 can be fixed to the inner tube 32.

As shown in FIG. 2 to FIG. 4, the balloon body 20 has a protrusion part 60 that projects outwardly in the radial direction y from the outer surface of the balloon body 20 and extends in the longitudinal axis direction x in the straight tubular part 23 and the proximal tapered part 22. The maximum length of the protrusion part 60 projecting outwardly in the radial direction y from the outer surface of the balloon body 20 in a cross section in the radial direction y is preferably 1.2 times or more the film thickness of the balloon body 20, more preferably 1.5 times or more, even more preferably 2 times or more, and is acceptable to be 100 times or less, 50 times or less, 30 times or less, or 10 times or less. The maximum length may differ in the longitudinal direction x. The protrusion part 60 having the maximum length in the above range makes it easier to make an incision of appropriate depth in the stenosis to easily dilate it. In addition, the protrusion part 60 disposed on the balloon body 20 makes it possible to improve the strength of the balloon 2 and prevent overinflation of the balloon 2 when pressurized.

As shown in FIG. 1 and FIG. 2, the balloon body 20 may be configured with the protrusion part 60 also in the proximal sleeve part 21 by extending the protrusion part 60 located in the proximal tapered part 22 to the proximal sleeve part 21. Alternatively, although not shown in the figures, the balloon body 20 may be configured without the protrusion part 60 in the proximal sleeve part 21.

As shown in FIG. 3 and FIG. 4, the number of the protrusion part 60 in the circumferential direction z may be more than one, or may be one as shown in FIGS. 5 to 9. When more than one protrusion part 60 are disposed in the circumferential direction z, each protrusion part 60 is preferably spaced apart from each other in the circumferential direction z, and more preferably equally spaced in the circumferential direction z. The distance between each of the protrusion part 60 is preferably longer than the maximum circumference of the protrusion part 60. A plurality of the protrusion part 60, each of which is spaced apart in the circumferential direction z, preferably equally spaced, allows the balloon 2 to be easily fixed and facilitate incision of the stenosis.

The protrusion part 60 extending in the longitudinal direction x on the outer surface of the balloon body 20 may be arranged at the same position in the circumferential direction z along the longitudinal direction x, i.e., straight in the longitudinal direction x as shown in FIG. 2, The protrusion part 60 straightly arranged can incise the stenosis straightly. Alternatively, although not shown in the figures, the protrusion part 60 may be arranged at different positions in the circumferential direction z along the longitudinal axis direction x, e.g., in a helical arrangement around the outer surface of the balloon body 20 in the circumferential direction z. With such a protrusion part 60, the stenosis can be incised obliquely.

The ratio of the height $H_1$ of the protrusion part 60 and the width $W_1$ of the protrusion part 60 in the straight tubular part 23 is greater than the ratio $W_2/H_2$ of the height $H_2$ of the protrusion part 60 and the width $W_2$ of the protrusion part 60 in the proximal tapered part 22. The height of the protrusion part 60 is a difference between a radius $r_b$ of a circumscribed circle $C_b$ of the balloon body 20 and a radius $r_p$ of a circumscribed circle $C_p$ of the protrusion part 60 that shares the center O with the circumscribed circle $C_b$ in a cross section in the radial direction y; and the width of the protrusion part 60 is a maximum length of an arc inside the outline of the protrusion part 60 among circumferences of concentric circles $C_c$ that shares the center O with the circumscribed circle $C_b$ in a cross section in the radial direction y.

The definition of the height of the protrusion part 60 is explained referring to FIG. 5 to FIG. 9. FIG. 5 is a cross-sectional view in the radial direction y of the straight tubular part 23 of the balloon 2 in accordance with one embodiment. In the embodiment shown in FIG. 5, the circumscribed circle $C_b$ coincides with the circumference of the balloon body 20 because the circumference of the balloon body 20 has a circular shape. Since the circumscribed circle $C_p$ of the protrusion part 60 that shares the center O with the circumscribed circle $C_b$ is uniquely determined, the height $H_1$ of the protrusion part 60 in the straight tubular part 23 can be obtained by calculating the difference between the radius $r_p$ of the circumscribed circle $C_p$ and the radius $r_b$ of the circumscribed circle $C_b$.

FIG. 6 is a cross-sectional view in the radial direction y in the proximal tapered part 22 of the balloon 2 in accordance with another embodiment. In the embodiment shown in FIG. 6, the circumscribed circle $C_b$ is different from the circumference of the balloon body 20 because the circumference of the balloon body 20 deviates from a circular shape by becoming an oval-like shape that is long in the direction of the protrusion part 60 due to the thicker film thickness of the balloon body 20 at the portion where the protrusion part 60 is located in the circumferential direction z. Even in such a case, since the circumscribed circle $C_p$ of the protrusion part 60 that shares the center O with the circumscribed circle $C_p$ is uniquely determined, the height $H_1$ of the protrusion part 60 in the straight tubular part 23 can be obtained by calculating the difference between the radius $r_p$ of the circumscribed circle $C_p$ and the radius $r_b$ of the circumscribed circle $C_b$. The circumference of the balloon body 20 may deviate from a circular shape because the film thickness of the balloon body 20 varies in the circumferential direction z in a cross section in the radial direction y, as shown in FIG. 6. Alternatively, although not shown in the figures, the circumference of the balloon body 20 may deviate from a circular shape because the cross-sectional shape of the balloon body 20 itself deviates from a circular shape, although the film thickness of the balloon body 20 is the same in the circumferential direction z in a cross section in the radial direction y.

FIG. 7 is a cross-sectional view in the radial direction y in the proximal tapered part 22 of the balloon 2 in accordance with one embodiment. In the embodiment shown in FIG. 7, the circumscribed circle $C_b$ coincides with the circumference of the balloon body 20 because the circumference of the balloon body 20 has a circular shape. Since the circumscribed circle $C_p$ of the protrusion part 60 that shares the center O with the circumscribed circle $C_b$ is uniquely determined, the height $H_2$ of the protrusion part 60 in the proximal tapered part 22 can be obtained by calculating the difference between the radius $r_p$ of the circumscribed circle $C_p$ and the radius $r_b$, of the circumscribed circle $C_b$. Although not shown in the figures, as described in the above explanation about the straight tubular part 23 referring to FIG. 6, even in a case where the circumference of the balloon body 20 deviates from a circular shape, since the circumscribed circle $C_b$ and the circumscribed circle $C_p$ are uniquely determined, the height $H_2$ of the protrusion part 60 in the proximal tapered part 22 can be obtained by calculating the difference between the radius r p of the circumscribed circle $C_p$ and the radius $r_b$ of the circumscribed circle Ch.

FIG. 8 and FIG. 9 are cross-sectional views in the radial direction y in the proximal tapered part 22 of the balloon 2 in accordance with different embodiments, respectively. In the embodiments shown in FIG. 8 and FIG. 9, the cross-sectional shape of the protrusion part 60 in the cross section in the radial direction y is different from that in the embodiment shown in FIG. 7. Even in such a case, since the circumscribed circle $C_b$ and the circumscribed circle $C_p$ are uniquely determined, the height $H_2$ of the protrusion part 60 in the proximal tapered part 22 can be obtained by calculating the difference between the radius $r_p$ of the circumscribed circle $C_p$ and the radius $r_b$ of the circumscribed circle $C_b$.

Next, the definition of the width of the protrusion part 60 is explained referring to FIG. 5 to FIG. 9. As shown in FIG. 5, the width of the protrusion part 60 is the maximum length of an arc inside the outline of the protrusion part 60 among circumferences of concentric circles $C_c$ that shares the center O with the circumscribed circle $C_b$ in a cross-section in the radial direction y of the straight tubular part 23. While there are infinite number of concentric circles $C_c$ that share the center O with the circumscribed circle $C_b$, among them, there is a finite number of concentric circles $C_c$ whose circumference lies partly inside the outline of the protrusion part 60. Furthermore, among them, at least one concentric circle $C_c$ can be determined such that the length of its arc that exists inside the outline of the protrusion part 60 becomes the largest, and the length of the arc can be determined as the width $W_1$ of the protrusion part 60 of the straight tubular part 23. In the embodiment shown in FIG. 5, the protrusion part 60 is at its widest at the base side closest to the center O, and the concentric circle $C_c$, where the length of the arc inside the outline of the protrusion part 60 is longest, coincides with the circumscribed circle $C_b$ of the balloon body 20.

In the embodiment shown in FIG. 6, the protrusion part 60 is also at its widest at the base side closest to the center O, and the concentric circle $C_c$, where the length of the arc inside the outline of the protrusion part is longest, coincides with the circumscribed circle $C_b$ of the balloon body 20. In addition to these examples, although not shown in the figures, even when the protrusion part 60 has a maximum width other than at the base side, at least one concentric circle $C_c$ that shares the center O with the circumscribed circle $C_b$ and has the longest arc inside the outline of the protrusion part 60 can be determined, thereby, the width $W_1$ of the protrusion part 60 in the straight tubular part 23 can be obtained.

The width $W_2$ of the protrusion part 60 in the proximal tapered part 22 can be obtained in the same way as the width $W_1$ of the protrusion part 60 in the straight tubular part 23. While the cross-sectional shape of the protrusion part 60 in the cross section in the radial direction y is different in each case of the embodiments shown in FIG. 7 and FIG. 8, the width $W_2$ of the protrusion part 60 can be obtained in the same way as for the straight tubular part 23 shown in FIG. 5. In the embodiments shown in FIG. 7 and FIG. 8, the protrusion part 60 is at its widest at the base side closest to the center O, and the concentric circle $C_c$, where the length of the arc inside the outline of the protrusion part 60 is longest, coincides with the circumscribed circle of the balloon body 20 as in FIG. 5.

The embodiment shown in FIG. 9 is an example of a case in which the protrusion part 60 has the maximum width other than at the base side, in this case, while the concentric circle $C_c$, where the length of the arc inside the outline of the protrusion part 60 is longest, is different from the circumscribed circle $C_b$ of the balloon body 20, the width $W_2$ of the protrusion part 60 can be obtained since at least one concentric circle $C_c$ that has the longest arc inside the outline of the protrusion part 60 can be determined.

The cross-sectional shape of the protrusion part 60 in the radial direction y may be any shape, and may be approximate triangle as shown in FIGS. 3 to 7, may be approximate pentagonal as shown in FIG. 8 and FIG. 9, or may be polygon, fan shape, wedge shape, convex shape, spindle shape, circular shape, or the like. Whatever the cross-sectional shape of the protrusion part 60 in the radial direction y, the height and width of the protrusion part 60 can be determined by the above definition.

The ratio $W_1/H_1$ of the height $H_1$ of the protrusion part 60 and the width $W_1$ of the protrusion part 60 in the straight tubular part 23 determined as above is greater than the ratio $W_2/H_2$ of the height $H_2$ of the protrusion part 60 and the width $W_2$ of the protrusion part 60 in the proximal tapered part 22, which makes the width $W_1$ of the protrusion part in the straight tubular part 23 relatively larger than the height $H_1$, thereby widening the area that can be incised by the protrusion part 60 in the circumferential direction z, making the balloon capable of efficient incision when inflated. In addition, the ratio $W_1/H_1$ of the protrusion part 60 in the straight tubular part 23 is relatively large, i.e., the height $H_1$ of the protrusion part 60 is relatively smaller than the width $W_1$ in the straight tubular part 23, which can make the outer diameter of the balloon 2 relatively small when deflated and facilitate insertion of the balloon 2 in the body cavity. Furthermore, the deflation time is shortened because the stiffness of the balloon 2 is reduced and the balloon 2 can be easily deflated, thereby shortening the treatment time when multiple dilatations are performed and reducing the time required to remove the deflated balloon after dilatation or to transport it to another lesion, resulting in safer and less burdensome treatment for the patient.

The ratio $W_1/H_1$ of the height $H_1$ of the protrusion part 60 and the width $W_1$ of the protrusion part 60 in the straight tubular part 23 is greater than the ratio $W_2/H_2$ of the height $H_2$ of the protrusion part 60 and the width $W_2$ of the protrusion part 60 in the proximal tapered part 22, i.e., the ratio $W_2/H_2$ of the height $H_2$ and the width $W_2$ of the protrusion part 60 in the proximal tapered part 22 is relatively smaller, which can make the height $H_2$ of the protrusion part 60 relatively larger than the width $W_2$ in the proximal tapered part 22. Thereby, the bending stiffness of the proximal tapered part 22 in the longitudinal axis direction x is increased compared to the straight tubular part 23, allowing the balloon 2 to have good pushability. In addition, the ratio $W_2/H_2$ of the height $H_2$ and the width $W_2$ of the protrusion part 60 in the proximal tapered part 22 is relatively small, i.e., the width $W_2$ of the protrusion part 60 is relatively smaller than the height $H_2$, which narrows the area that is a three-dimensional obstacle in the circumferential direction z when the balloon 2 is inserted into the body cavity, facilitating insertion of the balloon 2 in the body cavity.

Thus, the bending stiffness of the balloon 2 can decrease in the longitudinal axis direction x from the proximal to the distal side of the balloon 2, so that the balloon as a whole has an optimal balance of bending stiffness, good pushability, and good kink resistance and insertion.

The width $W_1$ of the protrusion part 60 in the straight tubular part 23 is preferably wider than the width $W_2$ of the protrusion part in the proximal tapered part 22. The relatively wider width $W_1$ of the protrusion part 60 in the straight tubular part 23 widens the area that can be incised by the protrusion part 60 of the straight tubular part 23 in the circumferential direction z, increasing the dilatation force during incision, making it easier to make the balloon 2 capable of efficient incision. In addition, the relatively narrower width $W_2$ of the protrusion part 60 in the proximal tapered part 22 can narrow the area of three-dimensional obstruction in the circumferential direction z when the balloon 2 is inserted into the body cavity, making it easier to insert the balloon 2 into the body cavity.

The ratio $W_1/H_1$ in the straight tubular part 23 is preferably 0.2 or greater and 5 or smaller. The ratio $W_2/H_2$ in the straight tubular part 23 may be 0.4 or greater, 0.6 or greater, 0.8 or greater, 0.9 or greater, 1.0 or greater, 1.2 or greater, 1.25 or greater, 1.3 or greater, 1.5 or greater, or 2 or greater. The ratio $W_1/H_1$ in the straight tubular part 23 may be 4 or smaller, 3.5 or smaller, or 3 or smaller.

The ratio $W_2/H_2$ in the proximal tapered part 22 is preferably 0.2 or greater and 5 or smaller. The ratio $W_2/H_2$ in the proximal tapered part 22 may be 0.3 or greater, 0.4 or greater, 0.5 or greater, or 0.8 or greater. The ratio $W_2/H_2$ in the proximal tapered part 22 may be 3 or smaller, 2 or smaller, 1.5 or smaller, 1.2 or smaller, or 1.1 or smaller, and more preferably 1.0 or smaller, and even more preferably 0.9 or smaller.

In addition to satisfying the requirement that the ratio in the straight tubular part 23 is greater than the ratio $W_2/H_2$ in the proximal tapered part 22, the ratio $W_1/H_1$ in the straight tubular part 23 and the ratio $W_2/H_2$ in the proximal tapered part 22 having the value in the above range, respectively, can further improve incision efficiency, pushability, and insertion in the body cavity.

As shown in FIG. 10, the protrusion part 60 of the straight tubular part 23 has a tip part 61 in a cross section in the radial direction y, and a ratio $W_1/H_1$ of a width $W_T$ of the tip part 61 of the protrusion part 60 and the width $W_1$ of the protrusion part 60 is preferably 0.5 or smaller. The width $W_T$ of the tip part 61 is defined as a length of an arc that is inside the outline of the protrusion part 60 and is a part of the circumference of the concentric circle C that has a radius of 95% of the radius $r_p$ of the circumscribed circle $C_p$ and shares the center O with the circumscribed circle $C_p$ in a cross section in the radial direction y. The ratio $W_T/W_1$ of the width $W_T$ of the tip part 61 and the width $W_1$ of the protrusion part 60 is more preferably 0.4 or smaller, even more preferably 0.3 or smaller, and particularly preferably 0.25 or smaller, and may be 0.2 or smaller, or 0.1 or smaller. The lower limit of the ratio $W_T/W_1$ of the width $W_T$ of the tip part 61 and the width $W_1$ of the protrusion part 60 is not particularly limited, and for example, may be 0.01. The width $W_T$ of the tip part 61 of the protrusion part 60 having the value in the above range allows the area of the tip part 61 of the protrusion part 60 in contact with the stenosis to be smaller when the balloon 2 is inflated at the lesion and the straight tubular part 23 contacts the stenosis, allowing a larger force to act on a smaller area, thereby increasing stress on the stenosis and making the incision of the stenosis easier.

In addition to satisfying the requirement that the ratio $W_1/H_1$ in the straight tubular part 23 is greater than the ratio $W_2/H_2$ in the proximal tapered part 22, the height $H_1$ of the protrusion part 60 of the straight tubular part 23 is preferably 0.1 mm or higher. The height $H_1$ of the protrusion part 60 of the straight tubular part 23 is more preferably 0.2 mm or higher, even more preferably 0.3 mm or higher, and particularly preferably 0.4 mm or higher. The height $H_1$ of the protrusion part 60 of the straight tubular part 23 of the value in the above range can increase the stress on the stenosis by the tip part 61 of the protrusion part 60 when the straight tubular part 23 contacts the stenosis by inflating the balloon 2 at the lesion, thereby facilitating the incision of the stenosis. The height $H_1$ of the protrusion part 60 of the straight tubular part 23 is preferably 1 mm or lower, more preferably 0.8 mm or lower, even more preferably 0.7 mm or lower, and particularly preferably 0.6 mm or lower. The height $H_1$ of the protrusion part 60 of the straight tubular part

23 of the value in the above range allows for good insertion in the body cavity when transporting the balloon 2 to the lesion.

There is no need to increase the height $H_1$ of the protrusion part 60 of the straight tubular part 23 beyond the above upper limit, because the effect of the stress on the stenosis due to the height $H_1$ of the protrusion part 60 of the straight tubular part 23 is saturated above the upper limit described above. By satisfying the requirement that the ratio in the straight tubular part 23 is greater than the ratio $W_2/H_2$ in the proximal tapered part 22, rather than the effect of the height $H_1$ of the protrusion part 60 of the straight tubular part 23, the balloon 2 of the present invention can ensure that the stress exerted on the stenosis by the protrusion part 60 of the straight tubular part 23 can be applied in a wide range in the circumferential direction z. Thereby, the balloon 2 can be made to allow efficient incision with (good insertion without making the height $H_1$ of the protrusion part 60 of the straight tubular part 23 higher than necessary.

The height $H_2$ of the protrusion part 60 of the proximal tapered part 22 is preferably higher than the height $H_1$ of the protrusion part 60 of the straight tubular part 23, This improves the bending stiffness of the proximal tapered part 22 in the longitudinal axis direction x, resulting in good pushability, while the stiffness of the straight tubular part 23 can be reduced, allowing the balloon 2 to be easily deflated to make it easier to insert the balloon 2 in the body cavity. However, it is important that the above relationship between the height $H_2$ of the protrusion part of the proximal tapered part 22 and the height $H_1$ of the protrusion part 60 of the straight tubular part 23 is satisfied based on the requirement that the ratio $W_1/H_1$ in the straight tubular part 23 is greater than the ratio $W_2/H_2$ in the proximal tapered part 22. By satisfying said requirement, the balloon 2 can be made to have good pushability, easy insertion in the body cavity, and efficient incision of the stenosis.

As shown in FIG. 10, preferably, the protrusion part 60 of the straight tubular part 23 has the tip part 61 in a cross section in the radial direction y, and the tip part 61 has an angle θ of 135° or less. The angle θ is more preferably 120° or less, even more preferably 100° or less, and may be 90° or less, 80° or less, 60° or less, or 30° or less. The angle θ is preferably 5° or more, preferably 10° or more, and even more preferably 20° or more. The angle θ in the above range allows efficient incision.

As shown in FIG. 11, the protrusion part 60 of the straight tubular part 23 and the protrusion part 60 of the proximal tapered part 22 preferably extend continuously in the longitudinal axis direction x. The continuous extension of the protrusion part 60 in the longitudinal direction x from the proximal tapered part 22 to the straight tubular part 23 can improve the stiffness of the balloon 2 and prevent overinflation of the balloon 2 during pressurization, and can also further improve pushability.

As shown in FIG. 12, the distal tapered part 24 may have the protrusion part 60, and a height $H_3$ of the protrusion part 60 of the distal tapered part 24 is preferably lower than the height $H_1$ of the protrusion part 60 of the straight tubular part 23. Since the distal tapered part 24 is the leading portion when inserting the balloon 2 into the body cavity, the height $H_3$ of the protrusion part of the distal tapered part 24, which is kept low; can facilitate insertion of the balloon 2 into the body cavity by making the outer diameter of the distal tapered part 24 smaller. In the distal tapered part 24, the protrusion part 60 may be placed partially between the proximal and distal ends of the distal tapered part 24 in the longitudinal axis direction x, or may be placed in the entire range. From the viewpoint of facilitating insertion of the balloon 2 into the body cavity, the protrusion part 60 in the distal tapered part 24 is preferably placed partially in the longitudinal axis direction x, and in this case, preferably, the protrusion part 60 is placed on the proximal end side of the distal tapered part 24 and not placed on the distal end side of the distal tapered part 24. This allows the distal tapered part 24 to have a smaller outer diameter at its distal end side, making the balloon 2 easier to insert into the body cavity.

Like the proximal tapered part 22 and the straight tubular part 23, the distal tapered part 24 may have one or more protrusion parts 60. The protrusion part 60 of the straight tubular part 23 and the protrusion part of the distal tapered part 24 preferably extend continuously in the longitudinal axis direction x. The protrusion part 60 extending continuously in the longitudinal axis direction x from the straight tubular part 23 to the distal tapered part 24 can improve the stiffness of the balloon 2 and prevent overinflation of the balloon 2 during pressurization, and can also further improve pushability.

As shown in FIG. 13, the distal tapered part 24 preferably has an inner protrusion part 70 that projects inwardly in the radial direction y from the inner surface of the balloon body 20 and extends in the longitudinal axis direction x. This configuration allows the stiffness of the distal tapered part 24 to be improved and can prevent overinflation of the balloon 2 when pressurized by the inner protrusion part 70 that can reinforce the balloon body 20 from the inside, even if the height $H_3$ of the protrusion part 60 in the distal tapered part 24 is low. This can also further improve pushability. While FIG. 13 shows an embodiment with the protrusion part 60 in addition to the inner protrusion part 70, when the distal tapered part 24 has the inner protrusion part 70, the distal tapered part 24 may not have the protrusion part 60. Even without the protrusion part 60, the inner protrusion part 70 can improve the stiffness of the distal tapered part 24 and prevent overinflation of the balloon 2 when pressurized.

As shown in FIG. 13, the distal tapered part 24 has the protrusion part 60 and the inner protrusion part 70, and preferably, the protrusion part 60 and the inner protrusion part 70 of the distal tapered part 24 are arranged in the same position in the circumferential direction z. This allows the protrusion part 60 that can reinforce the balloon body 20 from the outside and the inner protrusion part 70 that can reinforce the balloon body 20 from the inside can reinforce the balloon body 20 in the distal tapered part 24 at the same position in the circumferential direction z, and thus, overinflation of the balloon 2 when pressurized can be further prevented.

Materials forming the balloon body 20 include, for example, polyolefin-based resin such as polyethylene, polypropylene, ethylene-propylene copolymer; polyester-based resin such as polyethylene terephthalate and polyester elastomer; polyurethane-based resin such as polyurethane and polyurethane elastomer, polyphenylene sulfide-based resin; polyamide-based resin such as polyamide and polyamide elastomer; fluorine-based resin; silicone-based resin; and natural rubber such as latex rubber. Only one of these may be used, or two or more may be used in combination. Of these, polyamide-based resin, polyester-based resin, and polyurethane-based resin are preferably used. In particular, elastomer resin is preferably used from the viewpoint of thinning and flexibility of the balloon body 20. For example, among polyamide-based resins, nylon 12, nylon 11, and the like are suitable for the resin forming the balloon body 20, and more preferably nylon 12 because it is relatively easy to mold when blow molding. Polyamide elastomers such as polyether ester amide elastomer and polyamide ether elastomer are also preferred in terms of thinning and flexibility of the balloon body 20. Of these, polyether ester amide elastomer is preferred in terms of high yield strength and good dimensional stability of the balloon body 20.

The protrusion part 60 is preferably composed of the same material as the balloon body 20. When the protrusion part 60 is made of the same material as the balloon body 20, the protrusion part 60 is less likely to damage the outer surface of the balloon body 20 while maintaining the flexibility of the balloon 2. The balloon body 20 and the protrusion part 60 are preferably integrally molded. This can prevent the protrusion part 60 from falling off from the balloon body 20.

In the embodiment in which the inner protrusion part 70 is disposed in the distal tapered part 24, preferably, the inner protrusion part 70 is also made of the same material as the balloon body 20 for the same reason as above.

The balloon 2 can be manufactured, for example, by placing a parison 200, as shown in FIG. 14, that is composed of resin and has a thick-walled portion 220 extending in the longitudinal direction x and placed at least a part of the circumferential direction z, in a mold having a groove in the lumen, and biaxially stretch-blow molding it. The protrusion part 60 can be formed, for example, by inserting the parison 200 into the lumen of the mold, allowing the thick-walled portion 220 of the parison 200 to enter the groove of the mold, and introducing fluid into the lumen 210 of the parison 200 to expand the parison 200. The width and height of the protrusion part 60 can be adjusted by the thickness of the thick-walled portion 220 of the parison 200 and the depth and shape of the groove of the mold. The distal tapered part 24 having the inner protrusion part 70 can be formed, for example, by pressing the thick-walled portion 220 of the parison 200 in the portion corresponding to the distal tapered part 24 against the portion of the mold with a shallow groove or no groove, and introducing fluid into the lumen 210 of the parison 200 to expand the parison 200. When the mold with the shallow groove in the portion is used, the configuration can be such that the protrusion part 60 and the inner protrusion part 70 are located at the same position in the circumferential direction z, and when the mold with no groove in the portion is used, the configuration can be such that the protrusion part 60 is not formed and the inner protrusion part 70 is formed. The above materials forming the balloon body 20 can be referred to for materials forming the parison 200.

Materials forming the shaft 3 include, for example, polyamide-based resin, polyester-based resin, polyurethane-based resin, polyolefin-based resin, fluorine-based resin, polyvinyl chloride-based resin, silicone-based resin, and natural rubber. Only one of these may be used, or two or more may be used in combination. Of these, the material forming the shaft 3 is preferably at least one of polyamide-based resin, polyolefin-based resin, and fluorine-based resin. This can improve surface slipperiness of the shaft 3 and improve the insertion of the balloon catheter 1 into the body cavity.

The balloon 2 and the shaft 3 may be joined by adhesive bonding, welding, or by attaching a ring-shaped member at the point where the end of the balloon 2 and the shaft 3 overlap to swage them. Of these, the balloon 2 and the shaft 3 are preferably joined by welding. By welding the balloon 2 and the shaft 3, the bond between the balloon 2 and the shaft 3 is difficult to be released even when the balloon 2 is repeatedly inflated and deflated, easily increasing the strength of the bond between the balloon 2 and the shaft 3.

A shown in FIG. 1, the balloon catheter 1 may be provided with a hub 4 at a proximal side of the shaft 3, and the hub 4 may be provided with a fluid inlet 7 that is connected to the flow channel of the fluid supplied to the interior of the balloon 2. In addition, the hub 4 preferably has a guidewire insertion port 5 that is connected to the guidewire insertion channel. The balloon catheter 1 having the hub 4 provided with the fluid inlet 7 and the guidewire insertion port 5 can facilitate the operation of supplying fluid inside the balloon 2 to inflate the balloon 2 and delivering the balloon 2 to a lesion site along a guidewire. The balloon 2 in accordance with embodiments of the present invention is applicable not only the so-called over-the-wire balloon catheter, as shown in FIG. 1, in which the guidewire is inserted over the distal to the proximal side of the shaft 3, but also applicable to a so-called rapid exchange balloon catheter, in which the guidewire is inserted from the distal side to the midway of the proximal side of the shaft.

The shaft 3 and the hub 4 may be joined by, for example, adhesive bonding or welding. Of these, the shaft 3 and the hub 4 are preferably joined by adhesive bonding. The adhesive bonding of the shaft 3 and the hub 4 can increase the bonding strength of the shaft 3 and the hub 4 to increase durability of the balloon catheter 1 when the materials forming the shaft 3 and the hub 4 are different, for example, in a case where the shaft 3 is made of material having high flexibility and the huh 4 is made of material having high stiffness.

The present application claims priority based on Japanese Patent Application No. 2021-41378 filed on Mar. 15, 2021. All the contents described in Japanese Patent Application No. 2021-41378 filed on Mar. 15, 2021 are incorporated herein by reference.

DESCRIPTION OF REFERENCE SIGNS

1: balloon catheter
2: balloon
3: shaft
4: hub
5: guidewire insertion port
7: fluid inlet
20: balloon body
21: proximal sleeve part
22: proximal tapered part
23: straight tubular part
24: distal tapered part
25: distal sleeve part
31: outer tube
32: inner tube
60: protrusion part
61: tip part
70: inner protrusion part
200: parison
210: lumen of parison
220: thick-walled portion of parison
$C_b$: circumscribed circle of balloon body
$r_b$: radius of circumscribed circle of balloon body
$H_1$: height of protrusion part in straight tubular part
$H_2$: height of protrusion part in proximal tapered part
$H_3$: height of protrusion part in distal tapered part
$W_1$: width of protrusion part in straight tubular part
$W_2$: width of protrusion part in proximal tapered part
$W_T$: width of tip part of protrusion part in straight tubular part
x: longitudinal axis direction
y: radial direction
z: circumferential direction

The invention claimed is:

1. A balloon for a balloon catheter, comprising:
a balloon body having an outer surface and an inner surface and extending from a proximal side to a distal side in a longitudinal axis direction, wherein the balloon body has a straight tubular part, a proximal tapered part located proximal to the straight tubular part, and a distal tapered part located distal to the straight tubular part,
the balloon body has a protrusion part that projects outwardly in a radial direction from the outer surface of the balloon body and extends in the longitudinal axis direction from the straight tubular part to the proximal tapered part, the radial direction is a direction extending from a center of a figure whose outline is an outer shape of the balloon body toward the outer surface of the balloon body in an inflated state in a cross section perpendicular to the longitudinal axis direction,
a ratio $W_1/H_1$ of a height $H_1$ of the protrusion part and a width $W_1$ of the protrusion part on the straight tubular part is greater than a ratio $W_2/H_2$ of a height $H_2$ of the protrusion part and a width $W_2$ of the protrusion part on the proximal tapered part, where the height of the protrusion part is a difference between a radius of a circumscribed circle $C_b$ of the balloon body and a radius of a circumscribed circle $C_p$ of the protrusion part that shares a center with the circumscribed circle $C_b$ in a radial cross section, and each of $W_1$ and $W_2$ of the protrusion part is a maximum length of an arc inside an outline of the protrusion part among circumferences of concentric circles that shares a center with the circumscribed circle $C_b$ in the radial cross section, and the width $W_1$ of the protrusion part in the straight tubular part is wider than the width $W_2$ of the protrusion part in the proximal tapered part.

2. The balloon for a balloon catheter according to claim 1, wherein the ratio $W_1/H_1$ on the straight tubular part is 0.2 or greater and 5 or smaller.

3. The balloon for a balloon catheter according to claim 1, wherein the ratio $W_2/H_2$ on the proximal tapered part is 0.2 or greater and 5 or smaller.

4. The balloon for a balloon catheter according to claim 1, wherein the protrusion part of the straight tubular part has a tip part in the radial cross section, and a ratio $W_T/W_1$ of a width $W_T$ of the tip part of the protrusion part and the width $W_1$ of the protrusion part is 0.5 or smaller, where the width of the tip part of the protrusion part is a length of an arc that is inside the outline of the protrusion part and is a part of a circumference of a concentric circle that has a radius 95% of the radius of the circumscribed circle $C_p$ and shares the center with the circumscribed circle $C_p$ in the radial cross section.

5. The balloon for a balloon catheter according to claim 1, wherein the height $H_1$ of the protrusion part of the straight tubular part is at least 0.1 mm or higher.

6. The balloon for a balloon catheter according to claim 1, wherein the protrusion part of the straight tubular part has a tip part in the radial cross section, and the tip part has an angle of 135° or less.

7. The balloon for a balloon catheter according to claim 1, wherein the protrusion part of the straight tubular part and the protrusion part of the proximal tapered part extend continuously in the longitudinal axis direction.

8. The balloon for a balloon catheter according to claim 1, wherein the distal tapered part has the protrusion part, and a height $H_3$ of the protrusion part of the distal tapered part is lower than the height $H_1$ of the protrusion part of the straight tubular part.

9. The balloon for a balloon catheter according to claim 8, wherein the protrusion part of the straight tubular part and the protrusion part of the distal tapered part extend continuously in the longitudinal axis direction.

10. The balloon for a balloon catheter according to claim 1, wherein the distal tapered part has an inner protrusion part that projects inwardly in the radial direction from the inner surface of the balloon body and extends in the longitudinal axis direction.

11. The balloon for a balloon catheter according to claim 10, wherein the protrusion part further extends to the distal tapered part, and the protrusion part and the inner protrusion part of the distal tapered part are arranged in the same position in a circumferential direction, the circumferential direction being along an outer perimeter of the balloon body in the inflated state in a cross section in the radial direction.

12. The balloon for a balloon catheter according to claim 1, wherein the protrusion part is composed of the same material as the balloon body.

\* \* \* \* \*